United States Patent [19]

Helsley et al.

[11] Patent Number: 4,822,796
[45] Date of Patent: Apr. 18, 1989

[54] 1-((PHENOTHIAZIN-10-YL)ALKYL)-ALPHA-PHENYL-4-PIPERIDINEMETHANOLS AND PHARMACEUTICAL USE

[76] Inventors: Grover C. Helsley, P.O. Box 94, Pluckemin, N.J. 07978; Larry Davis, P.O. Box 129, Sergeantsville, N.J. 08857; Gordon E. Olsen, 8K Franklin Greens, Somerset, N.J. 08873

[21] Appl. No.: 56,199

[22] Filed: Jun. 1, 1987

[51] Int. Cl.[4] .................... A61K 31/54; C07D 417/06
[52] U.S. Cl. .................................. 514/225.5; 544/46
[58] Field of Search .......................... 544/46; 514/224

[56] References Cited

U.S. PATENT DOCUMENTS

| | | | |
|---|---|---|---|
| 3,063,996 | 11/1962 | Gordon | 544/46 X |
| 3,130,194 | 4/1964 | Jacob et al. | 544/46 |
| 3,305,547 | 2/1967 | Stack et al. | 544/46 |
| 3,445,464 | 5/1960 | Jucker et al. | 544/46 X |
| 3,985,811 | 10/1976 | Fontanella et al. | 568/809 |
| 4,018,922 | 4/1977 | Derible | 544/46 X |
| 4,021,552 | 5/1977 | Welstead et al. | 514/224 |

OTHER PUBLICATIONS

Burger's Medicinal Chemistry, 4th Ed., Part III, Chapter 56 (1979) pp. 873-888.
Johnson et al., Chemical Abstracts, vol. 92 (1980) 208923k.
Boswell et al., J. Med. Chem., vol. 21, No. 1 (1978) pp. 136-139.
Costall et al., J. Pharm. Pharmac., vol. 30 (1978) pp. 771-778.
Searle and Co., Chemical Abstracts, vol. 54 (1960) 22689f.
Sterling Drug Inc., Chemical Abstracts, vol. 55 (1961) 14486e.
Rhone-Poulenc, Chemical Abstracts, vol. 56 (1962) 4677g.
Costall et al., Chemical Abstracts, vol. 91 (1979) 13455f.

Primary Examiner—Richard L. Raymond

[57] ABSTRACT

1-[(phenothiazin-10-yl)alkyl]-α-phenyl-4-piperidinemethanols and methods for treating pain or psychosis utilizing compounds or compositions thereof are disclosed.

10 Claims, No Drawings

1-((PHENOTHIAZIN-10-YL)ALKYL)-ALPHA-PHENYL-4-PIPERIDINEMETHANOLS AND PHARMACEUTICAL USE

This invention relates to 1-[(phenothiazin-10-yl)alkyl]-α-phenyl-4-piperidinemethanols. More particularly, this invention relates to 1-[(phenothiazin-10-yl)alkyl]-α-phenyl-4-piperidinemethanols of the formula

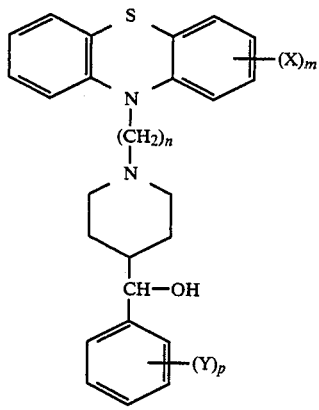

Formula I wherein X is a radical selected from the group consisting of halogen, trifluoromethyl, loweralkoxy, loweralkylthio, sulfamoyl, and dimethylsulfamoyl; Y is a radical selected from the group consisting of halogen, trifluoromethyl, loweralkyl, and loweralkoxy; m is an integer having a value of 0 or 1; n is an integer having a value from 2 to 4, inclusive; and p is an integer having a value from 0 to 2, inclusive.

Subgeneric to the compounds of this invention are compounds of the formula:

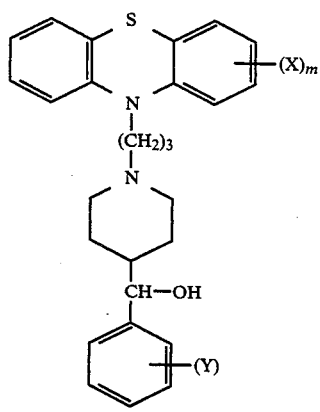

Formula II wherein X, Y, and m are as previously described.

As used throughout the specification and appended claims, the following definitions shall apply:

"Loweralkyl"—a straight or branched chain hydrocarbon radical containing no unsaturation and having from 1 to 6 carbon atoms inclusive such as, for example, methyl, ethyl, 1- and 2-propyl, 1-butyl, 1-pentyl, 2-pentyl, 3-hexyl, and the like. Preferred loweralkyls are those radicals having from 1 to 3 carbon atoms inclusive.

"Loweralkoxy"—a radical of the formula —O-loweralkyl such as, for example, methoxy, ethoxy, 1- and 2-propoxy, 1- and 2-pentoxy, 3-hexoxy, and the like.

Preferred loweralkoxys are those radicals having from 1 to 3 carbon atoms inclusive.

"Loweralkylthio"—a radical of the formula —S-loweralkyl such as, for example, methylthio, ethylthio, 1- and 2-propylthio, 1-butylthio, 1- and 2-pentylthio, 3-hexylthio, and the like. Preferred loweralkylthios and those radicals having from 1 to 3 carbon atoms inclusive.

"Halogen"—a member of the group consisting of fluorine, chlorine, and bromine radicals. Preferred halogens are chlorine or bromine.

The 1-[(phenothiazin-10-yl)alkyl]-α-phenyl-4-piperidinemethanols of this invention are prepared by treating a 1-[(phenothiazin-10-yl)alkyl]-4-benzoylpiperidine of the formula:

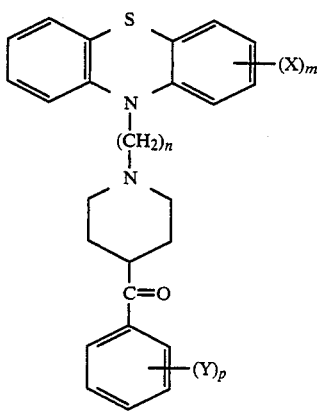

Formula III with an appropriate reducing agent. Among the suitable reducing agents there may be mentioned alkali metal borohydrides such as, for example, lithium borohydride, sodium borohydride and potassium borohydride. Sodium borohydride is preferred. The reduction is ordinarily carried out in the presence of an alkanol or a mixture of alkanols at a temperature of from about 0° to about 50° C., preferably from about 0° to about 25° C. Suitable alkanols include methanol, ethanol, 1- and 2-propanol, and the like. Mixtures of methanol and ethanol are preferred.

1-[(Phenothiazin-10-yl)alkyl]-4-benzoylpiperidines are prepared according to processes which are well known in the art and are described, for example, in U.S. Pat. No. 4,021,552 issued on May 3, 1977 to Welstead, Jr. et al., incorporated herein by reference. Pursuant to one conventional synthesis, 1-[(phenothiazin-10-yl)alkyl]-4-benzoylpiperidines are prepared by reacting a 4-benzoylpiperidine of the formula:

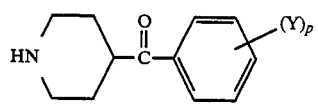

wherein Y and p are as previously described, with a 10-(haloalkyl)phenothiazine of the formula

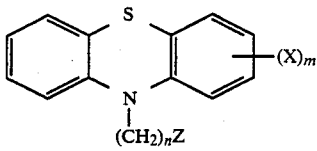

wherein X, m and n are as previously described and Z is chlorine, bromine or iodine, preferably chlorine. The reaction is conducted in a suitable inert organic solvent, in the presence of an acid acceptor, at a temperature of from about 70° C. to about 130° C., preferably from about 70° C. to about 90° C. Suitable solvents for this reaction include aromatic hydrocarbons such as, for example, benzene, xylene, toluene, and the like; as well as polar aprotic solvents such as, for example, dimethylformamide, dimethylacetamide, dimethylsulfoxide, hexamethylphosphoramide, and the like; dimethylformamide is preferred. As acid acceptors there may be mentioned inorganic bases including alkali metal hydroxides, carbonates and bicarbonates such as, for example, potassium hydroxide, sodium hydroxide, potassium carbonate, sodium carbonate, potassium bicarbonate and sodium bicarbonate. Sodium bicarbonate is preferred. Desirably, the reaction is conducted under anhydrous conditions.

Alternatively, 1-[(phenothiazin-10-yl)alkyl]-4-benzoylpiperidines may be prepared by reacting a 1-(haloalkyl)-4-benzoylpiperidine of the formula

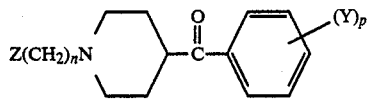

wherein Y, n and p are as previously described, and Z is chlorine, bromine or iodine, with a phenothiazine of the formula

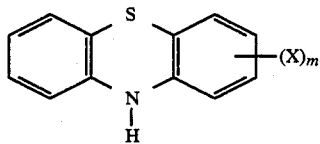

wherein X and m are as previously described, under conditions as described above for the reaction of a 10-(haloalkyl)phenothiazine with a 4-benzoylpiperidine.

Included among the compounds of this invention are:
1-[3-(phenothiazin-10-yl)propyl]-α-phenyl-4-piperidinemethanol;
α-(4-chlorophenyl)-1-[3-(phenothiazin-10-yl)propyl]-4-piperidinemethanol;
1-[3-(2-chlorophenothiazin-10-yl)propyl]-α-(4-fluorophenyl)-4-piperidinemethanol;
1-[2-(2-methoxyphenothiazin-10-yl)ethyl]-α-phenyl-4-piperidinemethanol;
α-(3-chlorophenyl)-1-[(2-(2-trifluoromethyl)phenothiazin-10-yl)ethyl]-4-piperidinemethanol;
1-[3-(2-methoxyphenothiazin-10-yl)propyl]-α-[4-(trifluoromethyl)phenyl]-4-piperidinemethanol;
α-(4-methylphenyl)-1-[4-(phenothiazin-10-yl)butyl]-4-piperidinemethanol;
α-(3-methoxyphenyl)-1-[4-(phenothiazin-10-yl)butyl]-4-piperidinemethanol;
1-[4-(2-methoxyphenothiazin-10-yl)butyl]-α-(4-methylphenyl)-4-piperidinemethanol;
1-[3-(3-ethoxyphenothiazin-10-yl)propyl]-α-(4-ethylphenyl)-4-piperidinemethanol;
α-phenyl-1-[3-(2-sulfamoylphenothiazin-10-yl)propyl]-4-piperidinemethanol;
1-[2-(2-dimethylsulfamoylphenothiazin-10-yl)ethyl]-α-phenyl-4-piperidinemethanol;
1-[2-(3-methylthiophenothiazin-10-yl)ethyl]-α-phenyl-4-piperidinemethanol;
1-[3-(2-ethylthiophenothiazin-10-yl)propyl]-α-(4-fluorophenyl)-4-piperidinemethanol;
α-(2,4-dichlorophenyl)-1-[3-(2-methoxyphenothiazin-10-yl)propyl]-4-piperidinemethanol; and
α-(2,4-dimethylphenyl)-1-[3-(3-fluorophenothiazin-10-yl)propyl]-4-piperidinemethanol.

1-[(phenothiazin-10yl)alkyl]-α-phenyl-4-piperidinemethanols of this invention are useful as analgetics as a result of their ability to alleviate pain in mammals.

The procedure employed to determine analgesic utility is a modification of the phenyl-p-quinone writhing assay in mice, a standard assay for analgesia [Proc. Soc. Exptl. Bio. Med., 95 729 (1957)]. In the modified procedure phenyl-p-benzoquinone (Eastman, 12.5 mg) is dissolved in 5 ml of 95% ethanol and the solution is diluted to a total volume of 100 ml with distilled water. The solution is administered to the subject mice subcutaneously at a dose of 10 ml per kg of body weight. A characteristic "writh", an inward rotation of one or more feet with twisting and turning of the trunk, drawing in of the abdominal wall, lordosis and arching of the back, is produced.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four groups of five animals (20 animals) are given the test compound subcutaneously at 15, 30, 45 and 60 minutes prior to administration of the phenyl-p-quinone. Four control groups of 2 animals (8 animals) receive an equal volume of the vehicle. After the administration of the phenyl-p-quinone, the mice are placed separately in one liter beakers, and after five minutes, are observed for ten minutes. The number of writhes for each animal is recorded. The following formula is used to compute the percent inhibition.

$$\frac{\bar{x} \text{ Writhes in Control Group} - \bar{x} \text{ Writhes in Drug Group}}{\bar{x} \text{ Writhes in Control Group}} \times 100$$

The time period with the greatest percent of inhibition is considered the peak time. A dose range determination is generally reserved for those compounds which inhibit writhing by greater than 65–70% at the screening dose.

A dose range determination is run in the same manner as the time response except 10 animals per group are tested at the peak time of test drug activity. Fifty animals, 4 test drug groups, and a vehicle control are employed. Animals are dosed and tested in a randomized manner. The ED$_{50}$ value, i.e., the calculated dose at which 50% inhibition of writhing is produced, is determined by a computer linear regression analysis. The calculated subcutaneous (s.c.) dose effecting an approximately 50% inhibition of writhing (ED$_{50}$) in mice produced in this assay is as follows:

| Compound | Analgesic Activity (% Inhibition of Writhing) |
|---|---|
| α-(4-Fluorophenyl)-1-[3-(2-methylthiophenothiazin-10-yl)-propyl]-4-piperidinemethanol | 43% at 20 mg/kg |
| Pentazocine (standard) | 50% at 1.3 mg/kg sc |

Analgesia production is achieved when the 1-[(phenothiazin-10-yl)alkyl]-α-phenyl-4-piperidinemethanols of this invention are administered to a subject requiring such treatment as an effective oral, parenteral or intravenous dose of from 0.1 to 50 mg/kg of body weight per day. 1-[(phenothiazin-10-yl)alkyl]-α-phenyl-4-piperidinemethanols which achieve effective analgesia production at doses of about 5 mg/kg of body weight per day are particularly desirable. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

As a result of their ability to elicit an antipsychotic response in mammals, the 1-[(phenothiazin-10-yl)alkyl]-α-phenyl-4-piperidinemethanols of this invention have utility as antipsychotics.

Antipsychotic activity is determined in the climbing mice assay by methods similar to those described by P. Protais, et al., Psychopharmacol, 50, 1 (1976) and B. Costall, Eur. J. Pharmacol., 50, 39 (1978).

The subject CK-1 male mice (23–27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected interaperitoneally (i.p.) 30 minutes prior to the apomorphine challenge at a screening dose of 10 mg/kg.

For evaluation of climbing, 3 readings are taken at 10, 20 and 30 minutes after apomorphine administration according to the following scale.

| Climbing Behavior Mice with: | Score |
|---|---|
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging onto the cage walls, rather motionless, over longer periods of time. By contrast, climbs due to mere motor stimulation usually last only a few seconds.

A dose range determination is generally reserved for those compounds inhibit climbing by greater than about 70% at the screening dose.

The climbing scores are individually totaled (maximum score: 6 per mouse over 3 readings) and the total score for the control group (vehicle interperitoneally-apomorphine subcutaneously) is set to 100%. ED$_{50}$ values i.e., the calculated dose at which 50% inhibition of apomorphine induced climbing is produced is calculated by linear regression analysis. The calculated interperitoneal (i.p.) dose effecting an approximately 50% inhibition of climbing (ED$_{50}$) in mice produced in this assay is as follows:

| Compound | Anti-Psychotic Activity (ED$_{50}$ mg/kg, i.p.) |
|---|---|
| α-(4-Fluorophenyl)-1-[3-(2-methylthiophenothiazin-10-yl)-propyl]-4-piperidinemethanol | 8.6 |
| Thioridazine (standard) | 4.1 |

Dosage levels at which the 1-[(phenothiazin-10-yl)alkyl]-α-phenyl-4-piperidinemethanols of this invention achieve an anti-psychotic response is subject to variation depending upon the particular compound employed. In general, an anti-psychotic response may be elicited and effective doses ranging from about 0.1 to about 50 mg/kg of body weight per day. It is to be understood, however, that for any particular subject, specific dosage regimens should be adjusted according to the individual need and the professional judgement of the person administering or supervising the administration of the aforesaid compound. It is to be further understood that the dosages set forth herein are exemplary only and they do not, to any extent, limit the scope or practice of the invention.

Effective amounts of the present invention may be administered to a subject by any one of various methods, for example, orally as in capsules or tablets, parenterally in the form of sterile solutions or suspensions, and in some cases intravenously in the form of sterile solutions. The 1-[(phenothiazin-10-yl)alkyl]-α-phenyl-4-piperidinemethanols of this invention, while effective themselves, may be formulated and administered in the form of their pharmaceutically acceptable addition salts for purposes of stability, convenience, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; and excipient such as starch or lactose, a disintegrating agent such as alginic acid, Promogel ™, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the preceding type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and nontoxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzylalcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following Example is for illustrative purposes only and is not to be construed as limiting the invention.

EXAMPLE

α-(4-Fluorophenyl)-1-[3-(2-methylthiophenothiazin-10-yl)propyl]-4-piperidinemethanol fumarate To a stirred, cooled (5° C.) mixture of 3.1 g of 1-[3-(2-methylthiophenothiazin-10-yl)propyl]-4-(4-fluorobenzyol)piperidine in 50 ml of ethanol and 25 ml of methanol was added 1.0 g of sodium borohydride. The reaction mixture was stirred at 5° C. for 30 minutes and then at ambient temperature for two hours. The mixture was then evaporated to a semi-solid which was suspended in 100 ml of water, stirred for 10 minutes, and extracted with ethyl acetate (2×). The organic layer was washed with water, dried over anhydrous sodium sulfate, filtered and concentrated. The residue was purified by high pressure liquid chromatography on a silica gel column, eluting with 10% methanol/dichloromethane. Concentration of the appropriate fractions yielded approximately 2.6 g of α-fluorophenyl-1-[3-(2-methylthiophenothiazin-10-yl)propyl]-4-piperidinemethanol, mp ~60° C. The free base was dissolved in 50 ml of warm ethanol and treated with 25 ml of a warm ethanolic solution of 0.6 g of fumaric acid. After stirring for five minutes the solution was diluted with 400 ml of diethyl ether to precipitate the corresponding fumarate salt. The salt was collected and dried to give 2.3 g (60%) of α-fluorophenyl-1-[3-(2-methylthiophenothiazin-10yl)propyl]-4-piperidinemethanol fumarate, mp 175°–176° C.

ANALYSIS: Calculated for $C_{28}H_{31}FN_2OS_2 \cdot C_4H_4O_4$: 62.93% C, 5.78% H, 4.59% N. Found: 62.78% C, 5.84% H, 4.51% N.

What is claimed is:

1. A compound of the formula

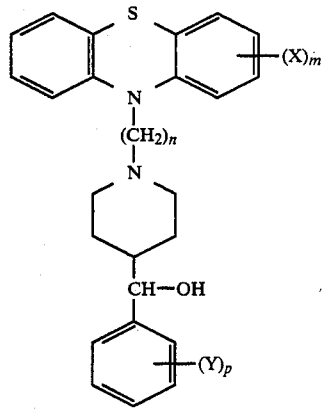

wherein X is a radical selected from the group consisting of halogen, trifluoromethyl, loweralkoxy, loweralkylthio, sulfamoyl, and dimethylsulfamoyl; Y is a radical selected from the group consisting of halogen, trifluoromethyl, loweralkyl and loweralkoxy; m is an integer having a value of 0 or 1; n is an integer having a value from 2 to 4 inclusive; and p is an integer having a value from 0 to 2 inclusive.

2. A compound as defined in claim 1 wherein n is 3 and p is 1.

3. A compound according to claim 2 wherein m is 0.

4. A compound according to claim 2 wherein m is 1 and X is alkoxy or alkylthio.

5. A compound according to claim 2 wherein m is 1 and X is halogen or trifluoromethyl.

6. A compound according to claim 2 wherein m is 1 and X is sulfamoyl or dimethylsulfamoyl.

7. The compound of claim 1 which is α-(4-fluorophenyl)-1-[3-(2-methylthiophenothiazin-10-yl)propyl]-4-piperidinemethanol.

8. A pharmaceutical composition comprising a pharmaceutically effective amount of a compound as defined in claim 1 or a pharmaceutically acceptable acid addition salt thereof and a carrier therefor.

9. A method of alleviating pain comprising administering to a mammal in need of pain alleviating, a pain alleviating effective amount of a compound as defined in claim 1.

10. A method of treating psychoses comprising administering to a mammal in need of psychoses treatment a psychoses treating effective amount of a compound as defined in claim 1.

* * * * *